United States Patent [19]

Knowles

[11] Patent Number: 5,889,039

[45] Date of Patent: *Mar. 30, 1999

[54] TOPICAL COMPOSITION FOR FUNGAL TREATMENT

[76] Inventor: W. Roy Knowles, 10919 Kemwood Dr., Houston, Tex. 77024

[ * ] Notice: The term of this patent shall not extend beyond the expiration date of Pat. No. 5,652,256.

[21] Appl. No.: 901,812

[22] Filed: Jul. 28, 1997

Related U.S. Application Data

[63] Continuation of Ser. No. 469,380, Jun. 6, 1995, Pat. No. 5,652,256.

[51] Int. Cl.⁶ ........................ A61K 31/135; A61K 31/415
[52] U.S. Cl. ............................................ 514/399; 514/657
[58] Field of Search ..................................... 514/399, 657

[56] References Cited

U.S. PATENT DOCUMENTS

| | | | |
|---|---|---|---|
| 4,537,776 | 8/1985 | Cooper | 514/244 |
| 4,602,011 | 7/1986 | West et al. | 514/187 |
| 4,766,113 | 8/1988 | West et al. | 514/187 |
| 4,859,696 | 8/1989 | Kamiya et al. | 514/420 |
| 4,863,970 | 9/1989 | Patel et al. | 514/784 |
| 4,948,588 | 8/1990 | Kamiya et al. | 424/436 |
| 5,026,556 | 6/1991 | Drust et al. | 424/449 |
| 5,053,227 | 10/1991 | Chiang et al. | 424/448 |
| 5,110,809 | 5/1992 | Wang et al. | 514/171 |
| 5,162,315 | 11/1992 | Rajadhyaksha et al. | 514/211 |
| 5,209,932 | 5/1993 | Nichols | 424/409 |
| 5,264,206 | 11/1993 | Bohn et al. | 424/61 |
| 5,304,551 | 4/1994 | Marples et al. | 514/182 |

FOREIGN PATENT DOCUMENTS

| | | |
|---|---|---|
| 503988 | 9/1992 | European Pat. Off. . |
| 2279623 | 11/1990 | Japan . |
| 93 08841 | 5/1993 | WIPO . |

OTHER PUBLICATIONS

Physician's Desk Reference, pp. 488 and 2492, 1994.

Riordan, Anne T., M.D., and Stiller, Matthew J., M.D., *Current Treatment of Onychomycosis*, The Journal of Geriatric Dermatology, Sep./Oct. 1994, vol. 2, No. 5, pp. 145–151.

Hermidy et al., J. of Applied Cosmetology, 12/4 pp. 73–84 (1994).

*Primary Examiner*—Phyllis Spivack
*Attorney, Agent, or Firm*—Jenkens & Gilchrist, P.C.

[57] ABSTRACT

A topical pharmaceutical composition having penetration enhancing properties for treating fungal dermatological conditions, comprising a pharmaceutically active topical antifungal agent selected from sulconazole and naftifine with an acetate penetration enhancing compound is disclosed.

3 Claims, No Drawings

TOPICAL COMPOSITION FOR FUNGAL TREATMENT

This is a continuation of copending application Ser. No. 08/469,380, filed Jun. 6, 1995, now U.S. Pat. No. 5,652,256.

FIELD OF THE INVENTION

This invention relates to a topical pharmaceutical composition having penetration enhancing properties for treating fungal dermatological conditions. Particularly, the composition has an enhanced ability to penetrate finger nails, toe nails, and the stratum cornea beneath nails.

BACKGROUND OF THE INVENTION

The risks associated with parenteral treatments, the concerns associated with variable rates of absorption and metabolism inherent in oral treatments, and difficulties in maintaining the continuity of drug administration can be avoided by relying upon efficacious topically applied compounds to treat certain maladies. Topical delivery allows effectively treating conditions which are local in nature, or which exhibit local manifestations, systemically, as well as locally with the same treatment regimen.

Dermatological pharmaceutically active agents are frequently applied topically to obtain desired results. Topical application in the form of creams, lotions, gels, and solutions, for example, may avoid systemic side effects and permits the application of high concentrations of the pharmaceutically active agent at the site of action. Some dermatological agents are applied topically for achieving a systemic effect and others are applied topically for achieving a situs effect.

Conditions such as onychomycosis pose serious problems in dermatology. Onychomycosis is a condition recognized by discoloration beneath toe nails and finger nails along with pain when pressure is placed near or at the site of discoloration. Various fungi, classified as white superficial fungi, cause the condition. Frequently the condition is treated by the combination of nail avulsion and pharmaceutical agent, as presently available topical anti-fungal formulations for treating onychomycosis have been met with limited success. This is primarily due to the limited ability of such compounds to penetrate into the nail plate, which is hyperkeratotic. The treatment of the condition is further problematic in geriatric patients where therapeutic options are often limited due to possible drug interactions, systemic side effects of treatment, and contra-indications secondary to other medical ailments.

Compounds known as penetration or permeation enhancers produce an increase in the permeability of skin or other body membranes to a pharmacologically active agent. The increased permeability allows an increase in the rate at which the drug permeates through the skin and enters the blood stream. Penetration enhancers have been successful in overcoming the impermeability of pharmaceutical agents through the skin. However, the thin stratum corneum layer of the skin, which is about 10 to 15 cells thick and is formed naturally by cells migrating toward the skin surface from the basal layer, has been found to be easier to penetrate than nails.

Penetration enhancers have been primarily categorized according to their ability to enhance permeation via three pathways. The first is the continuous polar or aqueous pathway composed of proteins. The second pathway is a continuous non-polar pathway consisting of lipids. The third pathway is a heterogenous polar-non-polar multilaminate of lipids and proteins.

Binary penetration systems comprising N-(2-hydroxyethyl) pyrrolidone in combination with a cell envelope disordering compound, such as oleic acid, enhances the penetration and percutaneous delivery of pharmaceutically active agents to human and animal tissue and systems. U.S. Pat. No. 4,537,776, Cooper, Aug. 27, 1985.

Anti-microbial compositions for controlling bacterial and fungal infections comprising a metal chelate of 8-hydroxyquinoline and an alkyl benzene sulfonic acid have been shown to be efficacious due to the increased ability of the oleophilic group to penetrate the lipid layers of microcells. The compounds however, do not effectively increase the ability to carry the pharmaceutically active anti-fungal through the cornified layer or stratum corneum of the skin. U.S. Pat. No. 4,602,011, West et al., Jul. 22, 1986; U.S. Pat. No. 4,766,113, West et al., Aug. 23, 1988.

Percutaneous absorption accelerators containing glycerols or polyglycerols and alcohols as essential components are known. U.S. Pat. No. 4,859,696, Kamiya et al., Aug. 22, 1989; U.S. Pat. No. 4,948,588, Kamiya et al., Aug. 14, 1990. The percutaneous absorbent preparations may be formulated by incorporating pharmaceutically effective anti-fungal components with the percutaneous absorbent accelerator. The percutaneous absorption accelerator can be advantageously used for many preparations of topical agents which are expected to exhibit the pharmacological effect to be absorbed from, for example, a liquid spraying agent, a lotion, an ointment, a cream, a gel, a sol, and aerosol, a cataplasm, a plaster, a tape preparation, and the like.

Other penetration enhancing pharmaceutical compositions for topical transepidermal and percutaneous application may contain an active pharmaceutical permeant, including hydrophilic salt forms. The hydrophilic salts are contained in a penetration enhancing vehicle comprising a cell envelope disordering compound. The formulation enhances the penetration of pharmaceutically active agents through the integument. U.S. Pat. No. 4,863,970, Patel et al., Sep. 5, 1989. It is also known to use compositions including diethylene glycol monoethyl or monomethyl ether in addition to an ester component to enhance the absorption of pharmaceutically active agents through the skin. U.S. Pat. No. 5,053,227, Chiang et al., Oct. 1, 1991.

Other compositions known for enhancing the transdermal delivery of pharmaceutically active agents may contain a polar solvent material and a polar lipid material. U.S. Pat. No. 5,026,556, Drust et al., Jun. 25, 1991. Compositions for carrying physiologically active agents through skin and for retaining these agents in body tissues may use a wide range of alkyl compounds to enhance penetration of such formulations. U.S. Pat. No. 5,162,315, Nov. 10, 1992.

The penetration enhancers discussed have been found to have limited potential for improving the permeability of finger nails and toe nails to pharmaceutically active agents. In order to overcome the highly impermeable nature of finger and toe nails, specifically selected vehicles or carriers to aid in the penetration of such compounds through nails must be found or developed. The successful treatment of persistent dermatological and other conditions which develop beneath nails will depend upon the ability of a penetration enhancer to allow a pharmaceutically active agent to pass through the thick, keratinized cell layers of the nails to attack the cause of the condition.

SUMMARY OF THE INVENTION

The present invention provides a topical pharmaceutical composition having penetration enhancing properties for treating fungal dermatological conditions, particularly the subungual condition known as onychomycosis. The composition comprises a pharmaceutically active topical antifungal agent hereinafter sometimes referred to as antifungal agent and a penetration enhancing compound.

Preferably the pharmaceutically active topical antifungal agent is naftifine hydrochloride. In alternate embodiments, sulconazole nitrate may be used. In yet other embodiments, the antifungal agent may be selected from the group of compounds consisting essentially of morpholines, allylamines, triazoles, and combinations thereof. The antifungal agent is often present in a gel or other carrier at an effective strength in the composition for topical application.

The preferred penetration enhancing compound is methyl acetate and is prepared in an amount of approximately 1 to 4 drops per 1 ounce of the topical antifungal agent. Acetate compounds that may be used as penetration enhancing compounds such as butylacetate, ethylacetate, isobutyl acetate, isopropyl acetate, propyl acetate or mixtures thereof. Other acetates may be used that are effective as penetration enhancers according to this invention. The penetration enhancing compound may be present in the pharmaceutically active topical anti-fungal in approximately 0.067% to 0.67% by weight of the pharmaceutically active topical anti-fungal. The topical pharmaceutical composition is preferably applied to a fungus affected nail area on a toe or finger or other affected area two times per day.

The penetration enhancing compound of the topical pharmaceutical composition improved the penetration ability of the pharmaceutically active topical antifungal agent through the finger and toe nails of patients. The improved penetration resulted in a greater amount of the antifungal reaching the situs of fungi causing the onychomycosis condition. Thus, the condition cleared more completely and during a shorter period of time than with other topical treatments.

DETAILED DESCRIPTION OF THE INVENTION

A topical pharmaceutical composition having penetration enhancing properties for treating fungal dermatological conditions was prepared by adding a penetration enhancing compound to a pharmaceutically active topical antifungal agent. The penetration enhancing composition is an acetate which can include methylacetate, ethylacetate, propylacetate, isopropylacetate, butylacetate or mixtures thereof. The preferred composition comprises four drops of the preferred penetration enhancing compound, methyl acetate, per one ounce of antifungal agent. The acetate is mixed into the antifungal agent until evenly dispersed therein. In alternate embodiments of the composition, one drop to 4 drops of the acetate may be added per one ounce of antifungal agent. The preferred range of acetate in the antifungal agent is from approximately 0.067%–0.67% by weight.

For the purpose of illustrating the present invention metylacetate was used in the studies presented. Methyl acetate was obtained from Spectrum Chemical Manufacturing Corporation, 14422 South San Pedro St., Gardena, Calif. 90249-9985. The preferred antifungal agent is naftifine hydrochloride 1% gel, having the chemical name (E)-N-Cinnamyl-N-methyl-1-naphthalene-methylamine hydrochloride. The pharmaceutical product NAFTIN® Gel, 1% (Allergan, Inc.) is preferred for use. In an alternate embodiment of the composition, sulconazole nitrate solution, 1%, having the chemical name (±)-1-[2,4-dichloro-β-[(p-chlorobenzyl)-thiol]-phenethyl] imidazole mononitrate, may be used. This compound is available as the product EXELDERM® solution, 1% (Westwood-Squibb).

In other alternate embodiments, fungicidal agents from the groups of compounds known as morpholines, allylamines, and triazoles may be used for the antifungal in the composition. These compounds have been shown to have promise in treating dermatological fungal conditions, including onychomycosis. Mixtures of the antifungal agents can be used in pharmaceutically active strengths. The compounds have effective fungicidal activity such that in the appropriate formulation which would allow the compound to reach the site of action, they may be effective in eradicating or controlling fungal conditions. Antifungal agents in the preferred and alternate embodiment may be used in liquid, lotion, ointment, cream, gel, aerosol, and other forms.

The efficacy of the preferred composition was observed and evaluated during a clinical study of 92 patients having onychomycosis. 45 of the patients were male and 47 were female. 46 of the patients were considered geriatric patients, being at least 60 years of age. Geriatric patients were sought to evaluate the effectiveness of treatment with the geriatric population due to the high incidence of dermatological conditions particularly, onychomycosis occurring in that group. Also, geriatric patients will frequently have thicker toe nails due to increased layers of keratinized cells, thereby making it even more difficult for topical preparations to penetrate.

Patients were initially selected for the study based upon clinical observation of the onychomycosis condition. Patients demonstrating the typical discoloration beneath toe nails associated with onychomycosis were tested to determine the presence of fungus. Toe nail scrapings were taken to identify the presence of the classification of fungus referred to as white superficial fungus, on and under the toe nails of the patients.

Toe nail scrapings were obtained using standard clinical procedures known to those skilled in the art. The scrapings were treated with potassium hydroxide (KOH) to dissolve the skin cells, leaving the fungal organisms. The KOH treated scrapings were viewed under microscopic conditions to verify the presence of the white superficial fungus. The procedures for performing the KOH evaluation are known to those in the art. Patients with a positive fungal presence were designated KOHT+.

The patients having toe nail scrapings testing KOH+were selected to participate in clinical observations to evaluate the effectiveness of the preferred embodiment of the composition. The toe nail scrapings were not cultured to identify specific fungal organisms.

The patients were instructed to apply two times per day the preferred composition of four drops of methyl acetate that had been mixed well in one ounce of the preferred antifungal agent naftifine hydrochloride-1% gel. The composition was massaged into the surface, particularly the nail, of the affected toes. The composition of the invention can be applied once every twenty-four hours to about twenty-four times every twenty-four hours. Application intervals of every 4 hours to every 12 hours are preferred. However, any treatment regimen which allows a safe and effective amount of the selected pharmaceutically active antifungal agent to reach the afflicted situs can be employed while using the compositions of this invention.

After 90 days of treatment, the onychomycosis was found to be fully cleared in the distal subungual of 66 patients (30 males and 36 females). The patients not showing complete clearing of the condition showed a visible improvement in the white superficial fungus condition of approximately 50%. It was observed that the condition cleared the sooner and to a greater extent in the female patients. No conclusion drawn from this observation.

The results observed with patients treated with the preferred embodiment of the composition comprising the pharmaceutically active topical antifungal agent and methyl acetate as the penetration enhancing vehicle were superior to those typically observed when onychomycosis is treated with known antifungal agents without methyl acetate. The antifungal agent with methyl acetate cleared the condition in 66 of the 100 patients completely in a shorter time than previously observed for partial clearing with other fungal agents not including methyl acetate. Results obtained with known onychomycosis treatment regimens are discussed in Riordan et al., *Current Treatment of Onychomycosis*, J. Geriatric Derm., Vol. 2, No. 5 (September/October 1994).

The percutaneous and subungual absorbability of pharmaceutically-effective antifungal compounds and such preparations is unsatisfactory. It is often difficult for a base alone, used for conventional topical agents, to attain percutaneous absorption sufficient for the pharmaceutically active components to be effective in completely or nearly completely eradicating fungal conditions in a short period of time. Previously available penetration enhancers have improved the penetration ability of pharmaceutical compounds through skin and other membranes, but have had limited success in improving the penetration of such compounds through nails.

It appears that the methyl acetate of the preferred embodiment of the topical pharmaceutical composition improved the penetration of the pharmaceutically active topical antifungal agent through the toe nails of patients. The improved penetration resulted in a greater amount of the antifungal reaching the situs of fungi causing the onychomycosis condition. Thus, the condition was cleared faster than with other topical treatments. The mechanism by which the methyl acetate improves the penetration of the antifungal agent through the toe nail is not known.

In any form of medical practice, there are many variables which affect the particular treatment regimen. In that regard, the final diagnosis and treatment of fungal conditions is left to the expertise of the practitioner and patient. A practitioner skilled in the art will be able to determine the application parameters of specific formulation and application based on the needs of the patient.

It will be obvious to those skilled in the art that the invention may be varied in many ways. Such variations are not to be regarded as a departure from the spirit and scope of the invention, and all such modifications as would be obvious to one skilled in the art are intended to be included within the scope of the claims.

I claim:

1. A topical pharmaceutical composition having penetration enhancing properties for treating fungal dermatological conditions comprising:
   a pharmaceutically active amount of a topical antifungal agent selected from the group of sulconalzole, naftifine and mixtures thereof; and
   an acetate penetration enhancing compound in the amount of approximately 0.067% to approximately 0.67% by weight.

2. A topical pharmaceutical composition having penetration enhancing properties for delivery of an anti fungal agent to toe nail and fingernail areas comprising
   a one percent gel of naftifine hydochloride; and
   methyl acetate evenly disparsed in the gel in a 0.067% to 0.67% by weight of methyl acetate to the gel composition.

3. A topical pharmaceutical composition having penetration enhancing properties for delivery of an antifungal agent to toe and fingernail areas comprising
   a 1% gel of sulconazole nitrate; and
   methyl acetate evenly dispersed through the gel in a 0.067% to 0.67% by weight of methyl acetate to the gel composition.

* * * * *